US010570465B1

(12) United States Patent
Etchebarne

(10) Patent No.: US 10,570,465 B1
(45) Date of Patent: *Feb. 25, 2020

(54) METHOD OF IMPROVED IDENTIFICATION OF AND ANTIBIOTIC RESISTANCE OF SEPSIS-RELATED MICROORGANISMS

(71) Applicant: Brett Eric Etchebarne, Okemos, MI (US)

(72) Inventor: Brett Eric Etchebarne, Okemos, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/361,718

(22) Filed: Mar. 22, 2019

Related U.S. Application Data

(63) Continuation of application No. 14/600,696, filed on Jan. 20, 2015, now Pat. No. 10,260,111.

(60) Provisional application No. 61/929,175, filed on Jan. 20, 2014.

(51) Int. Cl.
  *C12P 19/34* (2006.01)
  *C12Q 1/689* (2018.01)
  *C12N 15/10* (2006.01)
  *C12Q 1/6883* (2018.01)

(52) U.S. Cl.
  CPC ......... *C12Q 1/689* (2013.01); *C12N 15/1003* (2013.01); *C12Q 1/6883* (2013.01); *C12Q 2600/158* (2013.01)

(58) Field of Classification Search
  None
  See application file for complete search history.

(56) References Cited

U.S. PATENT DOCUMENTS

| | | | |
|---|---|---|---|
| 4,358,535 A | 11/1982 | Falkow et al. |
| 4,683,194 A | 7/1987 | Saiki et al. |
| 5,334,499 A | 8/1994 | Burdick et al. |
| 5,348,855 A | 9/1994 | Dattagupta et al. |
| 5,422,252 A | 6/1995 | Walker et al. |
| 5,470,723 A | 11/1995 | Walker et al. |
| 5,489,611 A | 2/1996 | Lee et al. |
| 5,532,128 A | 7/1996 | Eggers et al. |
| 5,543,292 A | 8/1996 | Imai et al. |
| 5,561,044 A | 10/1996 | Walker et al. |
| 5,624,825 A | 4/1997 | Walker et al. |
| 5,639,617 A | 6/1997 | Bohuon |
| 5,653,939 A | 8/1997 | Hollis et al. |
| 5,670,322 A | 9/1997 | Eggers et al. |
| 5,716,825 A | 2/1998 | Hancock et al. |
| 5,736,365 A | 4/1998 | Walker et al. |
| 5,811,269 A | 9/1998 | Nadeau et al. |
| 5,846,708 A | 12/1998 | Hollis et al. |
| 5,856,092 A | 1/1999 | Dale et al. |
| 5,882,863 A | 3/1999 | Imai et al. |
| 5,891,630 A | 4/1999 | Eggers et al. |
| 6,077,665 A | 6/2000 | Weirich et al. |
| 6,083,763 A | 7/2000 | Balch |
| 6,203,997 B1 | 3/2001 | Romaschin et al. |
| 6,268,148 B1 | 7/2001 | Barany et al. |
| 6,288,214 B1 | 9/2001 | Hook et al. |
| 6,306,590 B1 | 10/2001 | Mehta et al. |
| 6,312,892 B1 | 11/2001 | Barany et al. |
| 6,312,960 B1 | 11/2001 | Balch et al. |
| 6,331,441 B1 | 12/2001 | Balch et al. |
| 6,391,558 B1 | 5/2002 | Henkens et al. |
| 6,444,318 B1 | 9/2002 | Guire et al. |
| 6,451,311 B2 | 9/2002 | Althaus et al. |
| 6,465,206 B1 | 10/2002 | Collins |
| 6,479,301 B1 | 11/2002 | Balch et al. |
| 6,506,594 B1 | 1/2003 | Barany et al. |
| 6,525,102 B1 | 2/2003 | Chen et al. |
| 6,562,946 B2 | 5/2003 | Althaus et al. |
| 6,576,453 B2 | 6/2003 | Barany et al. |
| 6,632,682 B1 | 10/2003 | Ziegelmaier |
| 6,653,082 B2 | 11/2003 | Stockton |
| 6,689,473 B2 | 2/2004 | Guire et al. |
| 6,743,581 B1 | 6/2004 | Vo-Dinh |
| 6,756,483 B1 | 6/2004 | Bergmann et al. |
| 6,780,883 B2 | 8/2004 | Booth et al. |
| 6,790,611 B2 | 9/2004 | Lassen et al. |
| 6,797,470 B2 | 9/2004 | Barany et al. |
| 6,803,238 B1 | 10/2004 | Eggers |
| 6,852,487 B1 | 2/2005 | Barany et al. |
| 6,905,687 B2 | 6/2005 | Althaus et al. |
| 7,030,086 B2 | 4/2006 | Chen et al. |
| 7,083,917 B2 | 8/2006 | Barany et al. |
| 7,097,980 B2 | 8/2006 | Barany et al. |

(Continued)

OTHER PUBLICATIONS

Looft, Torey et al., "In-Feed Antibiotic Effects on the Swine Intestinal Microbiome", PNAS, vol. 109, No. 5, Jan. 31, 2012, pp. 1691-1696.

(Continued)

*Primary Examiner* — Kenneth R Horlick
(74) *Attorney, Agent, or Firm* — Howard & Howard Attorneys PLLC

(57) ABSTRACT

This disclosure provides a method for improving the efficiency and timing of detecting whether sepsis-related microorganisms are present in a fluid sample. The method comprises the steps of: collecting the fluid sample from a patient; fractioning the fluid sample to isolate a quantity of microorganism cells; extracting a portion of the microorganism cells from the fluid sample; lysing a portion of the microorganism cells extracted from the fluid sample to extract microorganism DNA; amplifying the microorganism DNA from the microorganism cells from a predetermined set of DNA primers to determine whether sepsis-related microorganisms are present within the fluid sample.

14 Claims, 5 Drawing Sheets

Specification includes a Sequence Listing.

(56) References Cited

U.S. PATENT DOCUMENTS

| | | |
|---|---|---|
| 7,132,246 B2 | 11/2006 | Bergmann et al. |
| 7,153,662 B2 | 12/2006 | Bergmann et al. |
| 7,156,969 B2 | 1/2007 | Mehta et al. |
| 7,157,081 B2 | 1/2007 | Bergmann et al. |
| 7,161,057 B2 | 1/2007 | Kneteman et al. |
| 7,166,434 B2 | 1/2007 | Barany et al. |
| 7,169,358 B2 | 1/2007 | Henkens et al. |
| 7,235,368 B2 | 6/2007 | Bergmann et al. |
| 7,244,619 B2 | 7/2007 | Contreras et al. |
| 7,244,831 B2 | 7/2007 | Barany et al. |
| 7,312,039 B2 | 12/2007 | Barany et al. |
| 7,320,865 B2 | 1/2008 | Barany et al. |
| 7,332,285 B2 | 2/2008 | Barany et al. |
| 7,338,770 B2 | 3/2008 | Althaus et al. |
| 7,354,774 B2 | 4/2008 | Hughes et al. |
| 7,361,724 B2 | 4/2008 | Guire et al. |
| 7,364,858 B2 | 4/2008 | Barany et al. |
| 7,413,850 B2 | 8/2008 | Bergmann et al. |
| 7,413,852 B2 | 8/2008 | Balch |
| 7,429,453 B2 | 9/2008 | Barany et al. |
| 7,455,965 B2 | 11/2008 | Barany et al. |
| 7,455,975 B2 | 11/2008 | Henkens et al. |
| 7,494,791 B2 | 2/2009 | Goel |
| 7,498,139 B2 | 3/2009 | Bergmann et al. |
| 7,498,479 B2 | 3/2009 | Kneteman et al. |
| 7,517,518 B2 | 4/2009 | Bergmann |
| 7,556,924 B2 | 7/2009 | Barany et al. |
| 7,569,209 B2 | 8/2009 | Bergmann |
| 7,572,590 B2 | 8/2009 | Bergmann |
| 7,579,172 B2 | 8/2009 | Cho et al. |
| 7,608,684 B2 | 10/2009 | Furusako et al. |
| 7,645,733 B2 | 1/2010 | Brines et al. |
| 7,659,075 B2 | 2/2010 | Bergmann |
| 7,723,492 B2 | 5/2010 | Bergmann et al. |
| 7,781,642 B2 | 8/2010 | Kneteman et al. |
| 7,807,142 B2 | 10/2010 | Chen et al. |
| 7,879,579 B2 | 2/2011 | Barany et al. |
| 7,888,099 B2 | 2/2011 | Gupta et al. |
| 7,892,746 B2 | 2/2011 | Barany et al. |
| 7,892,747 B2 | 2/2011 | Barany et al. |
| 7,893,233 B2 | 2/2011 | Barany et al. |
| 7,914,981 B2 | 3/2011 | Barany et al. |
| 7,915,013 B2 | 3/2011 | Cho et al. |
| 7,923,242 B2 | 4/2011 | Kono et al. |
| 7,939,282 B2 | 5/2011 | Fast et al. |
| 7,943,348 B2 | 5/2011 | Cho et al. |
| 7,972,799 B2 | 7/2011 | Bergmann et al. |
| 7,977,072 B2 | 7/2011 | Bergmann et al. |
| 7,998,686 B2 | 8/2011 | Bergmann et al. |
| 8,029,982 B2 | 10/2011 | Kingsmore et al. |
| 8,124,366 B2 | 2/2012 | Bergmann et al. |
| 8,124,722 B2 | 2/2012 | Furusako et al. |
| 8,183,004 B2 | 5/2012 | Bergmann et al. |
| 8,183,050 B2 | 5/2012 | Shi et al. |
| 8,187,805 B2 | 5/2012 | Matsuhisa et al. |
| 8,212,106 B2 | 7/2012 | Kneteman et al. |
| 8,221,995 B2 | 7/2012 | Lee et al. |
| 8,252,548 B2 | 8/2012 | Bergmann et al. |
| 8,283,121 B2 | 10/2012 | Barany et al. |
| 8,288,521 B2 | 10/2012 | Barany et al. |
| 8,298,774 B2 | 10/2012 | Bahrami et al. |
| 8,338,166 B2 | 12/2012 | Beer et al. |
| 8,354,506 B2 | 1/2013 | Bergmann et al. |
| 8,409,807 B2 | 4/2013 | Neely et al. |
| 8,426,180 B2 | 4/2013 | Bergmann et al. |
| 8,439,835 B1 | 5/2013 | McKinley et al. |
| 8,445,745 B2 | 5/2013 | Kneteman et al. |
| 8,450,463 B2 | 5/2013 | Bergmann et al. |
| 8,492,085 B2 | 7/2013 | Barany et al. |
| 8,507,210 B2 | 8/2013 | Bergmann et al. |
| 8,518,648 B2 | 8/2013 | Bjorck et al. |
| 8,546,110 B2 | 10/2013 | Ammann et al. |
| 8,569,019 B2 | 10/2013 | Ammann et al. |
| 8,569,020 B2 | 10/2013 | Ammann et al. |
| 8,597,890 B2 | 12/2013 | Barany et al. |
| 8,597,891 B2 | 12/2013 | Barany et al. |
| 8,614,572 B2 | 12/2013 | Florescu et al. |
| 8,624,016 B2 | 1/2014 | Barany et al. |
| 8,632,973 B2 | 1/2014 | Goel |
| 8,642,269 B2 | 2/2014 | Barany et al. |
| 8,669,113 B2 | 3/2014 | Shi et al. |
| 8,675,199 B2 | 3/2014 | Duer |
| 8,691,512 B2 | 4/2014 | Bergmann et al. |
| 8,697,370 B2 | 4/2014 | Kas et al. |
| 8,703,928 B2 | 4/2014 | Barany et al. |
| 8,735,079 B2 | 5/2014 | Bergmann et al. |
| 8,765,371 B2 | 7/2014 | Russwurm |
| 2006/0246495 A1 | 11/2006 | Garrett et al. |
| 2008/0114576 A1 | 5/2008 | Jackson et al. |
| 2008/0118491 A1 | 5/2008 | Cheng |
| 2009/0286691 A1 | 11/2009 | Kim et al. |
| 2011/0151453 A1 | 6/2011 | Bergeron et al. |
| 2011/0189654 A1 | 8/2011 | Himmelreich |
| 2011/0256527 A1 | 10/2011 | Messier et al. |
| 2011/0312758 A1 | 12/2011 | Azimi et al. |
| 2012/0295269 A1 | 11/2012 | Pourahmadi et al. |
| 2013/0084343 A1 | 4/2013 | Vilanova et al. |
| 2014/0211204 A1 | 7/2014 | Stedtfeld et al. |
| 2014/0329232 A1 | 11/2014 | Turba et al. |
| 2015/0247190 A1 | 9/2015 | Ismagilov et al. |
| 2015/0275276 A1 | 10/2015 | Wallach et al. |

OTHER PUBLICATIONS

Luo, Chengwei et al., "Genome Sequencing of Environmental *Escherichia coli* Expands Understanding of the Ecology and Speciation of the Model Bacteria Species", PNAS, vol. 108, No. 17, Apr. 26, 2011, pp. 7200-7205.

Lutz, Sascha et al., "Microfluidic Lab-On-A-Foil for Nucleic Acid Analysis Based on Isothermal Recombinase Polymerase Amplification (RPA)", Lap Chip, vol. 10, 2010, pp. 887-893.

Mancini, Nicasio et al., "The Era of Molecular and Other Non-Culture-Based Methods in Diagnosis of Sepsis", Clinical Microbiology Reviews, Jan. 2010, pp. 235-251.

Martin, Greg S. et al., "The Epidemiology of Sepsis in the United States From 1979 Through 2000", The New England Journal of Medicine, vol. 348, No. 16, Apr. 17, 2003, pp. 1546-1554.

Miller, Sarah M. et al., "In Situ-Synthesized Virulence and Marker Gene Biochip for Detection of Bacterial Pathogens in Water", Applied and Environmental Microbiology, vol. 74, No. 7, Apr. 2008, pp. 220-2209.

Misawa Yoshiki et al., "Application of Loop-Mediated Isothermal Amplification Technique to Rapid and Direct Detection of Methicillin-Resistant *Staphylococcus aureus* (MRSA) in Blood Cultures", J. Infect. Chemother, vol. 13, 2007, pp. 134-140.

Mueller, Paul R., et al., "In Vivo Footprinting of a Muscle Specific Enhancer by Ligation Mediated PCR", Science Magazine, Nov. 10, 1989, pp. 788-790.

National Institute of General Medical Sciences, "Sepsis Fact Sheet", Content Updated Sep. 2017, pp. 1-3.

Notomi, Tsugunori et al., "Loop-Mediated Isothermal Amplification of DNA", Nucleic Acids Research, vol. 28, No. 12, 2000, pp. i-vii.

Ochman, Howard et al., "Genetic Applications of an Inverse Polymerase Chain Reaction", Genetics Socieity of America, Genetics, vol. 120, Nov. 1988, pp. 621-623.

Oh, Seung Jun et al., "Centrifugal Loop-Mediated Isothermal Amplification Microdevice for Rapid, Multiplex and Colorimetric Foodborne Pathogen Detection", Biosensors and Bioelectronics, vol. 75, 2016, pp. 293-300.

Opal, Steven M. et al., "Antibiotic Usage and Resistance—Gaining or Losing Ground on Infectiions in Critically Ill Patients?", American Medical Association, 2009, pp. 2367-2368.

Parnell, J. Jacob et al,, "Coping with Polychlorinated Biphenyl (PCB) Toxicity: Physiological and Genome-Wide Responses of Burkholderia Xenovorans LB400 to PCB-Mediated Stress", Applied and Environmental Microbiology, vol. 72, No. 10, Oct. 2006, pp. 6607-6614.

(56) References Cited

OTHER PUBLICATIONS

Pavlov, Andrey R. et al., "Recent Developments in the Optimization of Thermostable DNA Polymerases for Efficient Applications", Trends in Biotechnology, vol. 22, No. 5, May 2004, pp. 253-260.
Piepenburg, Olaf et al., "DNA Detection Using Recombination Proteins", PLoS Biology, vol. 4, Issue 7, Jul. 2006, pp. 1115-1121.
Pierce, Kenneth E. et al., "Methods in Molecular Medicine: Single Cell Diagnostics: Methods and Protocols—Chaper 1: Linear-After-The-Exponential Polymerase Chain Reaction and Allied Technologies", Methods Mol. Med., vol. 132, 2007, pp. 65-85.
Poon, Leo L.M. et al., "Sensitive and Inexpensive Molecular Test for Falciparum Malaria: Detecting Plasmodium Falciparum DNA Directly from Heat-Treated Blood by Loop-Mediated Isothermal Amplification", Clinical Chemistry, vol. 52, 2006, pp. 303-306.
Prithiviraj, Jothikumar et al., "Rapid Detection of Microbial DNA by a Novel Isothermal Genome Exponential Amplification Reaction (GEAR) Assay", Biochemical and Biophysical Research Communications, vol. 420, 2012, pp. 738-742.
Procop, Gary W., "Molecular Diagnostics for the Detection and Characterization of Microbial Pathogens", Molecular Diagnostics, vol. 45, Suppl 2, 2007, pp. S99-S111.
Proquest "Drugs and Diagnostics for Hematological Disorders: Global Markets", PR Newswire, Jan. 2017, pp. 1-4.
Ramette, Alban et al., "Multiscale Responses of Microbial Life to Spatial Distance and Environmental Heterogeneity in a Patchy Ecosystem", PNAS, vol. 104, No. 8, Feb. 20, 2007, pp. 2761-2766.
Rivers, E.P. et al., "Early Interventions in Severe Sepsis and Septic Shock: A Review of the Evidence One Decade Later", Minerva Anestesiologica, Jun. 2012, pp. 712-724.
Rodriguez-Minguela, Carlos M. et al., "Worldwide Prevalence of Class 2 Integrases Outside the Clinical Setting is Associated with Human Impact", Applied and Environmental Micrbiology, vol. 75, No. 15, Aug. 2009, pp. 5100-5110.
Rossi, Ciro C. et al., "CRISPR-Cas Systems Features and the Gene-Reservoir Role of Coagulase-Negative Staphylococci", Frontiers in Microbiology, vol. 8, Article 1545, Aug. 2017, pp. 1-9.
Saiki, Randall K. et al., "Primer-Directed Enzymatic Amplification of DNA with a Thermostable DNA Polymerase", Science Magazine, vol. 239, No. 4839, Jan. 29, 1988, pp. 487-491.
Seo, Ja Young et al., "Laboratory Diagnosis of Clostridium Difficile Infection: Comparison of Techlab C. Diff Quik Chek Complete, Xpert C. Difficle, and Multistep Algorithmic Approach", J. Clin. Lab Anal., Dec. 13, 2016, pp. 1-5.
Shafazand, MD, Shirin et al., "Blood Cultures in the Critical Care Unit", CHEST, vol. 122, No. 5, Nov. 2002, pp. 1727-1736.
Silva, L.F.P. et al., "Intramammary Infusion of Leptin Decreases Proliferation of Mammary Epithelial Cells in Prepubertal Heifers", J. Dairy Sci., vol. 91, 2008, pp. 3034-2044.
Silva, L.F.P. et al., "Short Communication: Intamammary Infusion of IGF-I Increases Bromodeoxyuridine Labeling in Mammary Epithelial Cells of Prepubertal Heifers", J.Dairy Sci., vol. 88, 2005, pp. 2771-2773.
Stedtfeld, Rober D. et al.., "Gene-Z: A Device for Point of Care Genetic Testing Using a Smartphone", Lab Chip, vol. 12, 2012, pp. 1454-1462.
Stedtfeld, Robert D. et al., "Influence of Dangling Ends and Surface-Proximal Tails of Targets on Probe-Target Duplex Formation in 16S rRNA Gene-Based Diagnostic Arrays", Applied and Environmental Microbiology, vol. 73, No. 2, pp. 380-389, (2007).
Stedtfeld, Robert D. et al., "Static Self-Directed Sample Dispensing Into a Series of Reaction Wells on a Microfluidic Card for Parallel Genetic Detection of Microbial Pathogens", Biomed Microdevices, vol. 17, No. 89, 2015, pp. 1-12.
Stedtfeld, Robert D., "Development and Validation of a Multiplex Hand-Held Gene Analyzer—A Dissertation", Michigan State University, 2009, pp. 1-176.
Stedtfeld, Robert et al., "Development and Experiemental Validation of a Predictive Threshold Cycle Equation for Quantification of Virulence and Marker Genes by High-Throughput Nanoliter-Volume PCR on the OpenArray Platform", Applied and Environmental Microbiology, vol. 74, No. 12, Jun. 2008, pp. 3831-3838.
Stemmer, Willem P.C. et al., "Single-Step Assembly of a Gene and Entire Plasmid from Large Numbers of Oligodeoxyribonucleotides", Gene, vol. 164, 1995, pp. 49-53.
Sul, Woo Jun et al., "Bacterial Community Comparisons by Taxonomy-Supervised Analysis Independent of Sequence Alignment and Clustering", PNAS, vol. 108, No. 35, pp. 14637-14642, (2011).
Sun, Baolin et al., "Microbial Dehalorespiration with 1,1,1-Trichloroethane", Science Magazine, vol. 298, Nov. 1, 2002, pp. 1023-1025.
Tiedje, James et al., "Microbes in the Energy Grid", Science Magazine, vol. 320, May 23, 2008, p. 985.
Tourlousse, Dieter M. et al., "A Polymer Microfluidic Chip for Quantitative Detection of Multiple Water- and Foodborne Pathogens Using Real-Time Fluorogenic Loop-Mediated Isothermal Amplification", Biomed Microdevices, vol. 14, 2012, pp. 769-778.
Tsalik, Ephraim L. et al., "Multiplex PCR to Diagnose Bloodstream Infections in Patients Admitted from the Emergency Department with Sepsis", Journal of Clinical Microbiology, vol. 48, No. 1, Jan. 2010, pp. 26-33.
Van Der Zee, Anneke et al., "Molecular Diagnosis of Urinary Tract Infections by Semi-Quantitative Detection of Uropathogens in a Routine Clinical Hospital Setting", PLOS ONE, Mar. 8, 2016, pp. 1-10.
Van Doorn, Ronald et al., "Quantitative Multiplex Detection of Plant Pathogens Using a Novel Ligation Probe-Based System Coupled with Universal, High-Throughput Real-Time PCR on OpenArrays", BMC Genomics, vol. 8, No. 276, 2007, pp. 1-14.
Varani, Stefania et al., "Diagnosis of Bloodstream Infections in Immunocompromised Patients by Real-Time PCR", Journal of Infection, vol. 58, 2009, pp. 346-351.
Vincent, Jean-Louis et al., "International Study of the Prevalence and Outcomes of Infection in Intensive Care Units", JAMA, vol. 302, No. 21, Dec. 2, 2009, pp. 2323-2329.
Vincent, Jean-Louis et al., "The Prevalence of Nosocomial Infection in Intensive Care Unites in Europe", Concepts in Emergency and Critical Care, JAMA, vol. 274, No. 8, Aug. 23/30, 1995, pp. 639-644.
Vincent, Myriam et al., "Helicase-Dependent Isothermal DNA Amplification", EMBO Reports, vol. 5, No. 8, 2004, pp. 795-800.
Walk, Seth T. et al., "Cryptic Lineages of the Genus *Escherichia*", Applied and Environmental Microbiology, vol. 75, No. 20, Oct. 2009, pp. 6534-6544.
Wang, Qiong et al., "Naive Bayesian Classifier for Rapid Assignment of rRNA Sequences into the New Bacterial Taxonomy", Applied and Environmental Microbiology, vol. 73, No. 16, Aug. 2007, pp. 5261-5267.
Wang, Xuan et al., "Rapid and Sensitive Detection of Zika Virus by Reverse Transcription Loop-Mediated Isothermal Amplification", Journal of Virological Methods, vol. 238, 2016, pp. 86-93.
Watson, J. D., et al., Molecular Structure of Nucleic Acids, Nature, No. 4356, Apr. 25, 1953, pp. 737-738.
Wick, Lukas M. et al., "On-Chip Non-Equilibrium Dissociation Curves and Dissociation Rate Constants as Methods to Assess Specificity of Oligonucleotide Probes", Nucleic Acids Research, vol. 34, No. 3, 2006, pp. 1-10.
Workowski, Kimberly A. et al., "Emerging Antimicrobial Resistance in Neisseria Gonorrhoeae: Urgent Need to Strengthen Prevention Strategies" Annals of Internal Medicine, vol. 148, No. 8, Apr. 15, 2008, pp. 606-614.
Yager, Paul et al., "Point-of-Care Diagnostics for Global Health", Annu. Rev. Biomed. Eng., vol. 10, 2008, pp. 107-144.
Yan, Muxia et al., "Direct Detection of Various Pathogens by Loop-Mediated Isothermal Amplification Assays on Bacterial Culture and Bacterial Colony", Microbial Pathogens, vol. 102, 2017, pp. 1-7.
Yoder-Himes, Deborah et al., "Indentification of Potential Therapeutic Targets for Burkholderia Cenocepacia by comparative Transcriptomics", PLoS ONE, vol. 5, Issue 1, Jan. 2010, pp. 1-11.
Yoder-Himes, Deborah et al., "Mapping the Burkholderia Cenocepacia Niche Response via High-Throughput Sequencing", PNAS, vol. 106, No. 10, Mar. 10, 2009, pp. 3976-3981.

(56) References Cited

OTHER PUBLICATIONS

Zhu, Yong-Guan et al., "Diverse and Abundant Antibiotic Resistance Genes in Chinese Swine Farms", PNAS, vol. 110, No. 9, Feb. 26, 2013, pp. 3435-3440.

Zietkiewicz, Ewa et al., "Genome Fingerprinting by Simple Sequence Repeat (SSR)-Anchored Polymerase Chain Reaction Amplification", Genomics, vol. 20, 1994, pp. 176-183.

Becker, K. et al., "Coagulase-Negative Staphylococci", Clin Microbiol Rev, vol. 27, No. 4, Oct. 2014, pp. 870-926.

Biomerieux, "FilmArray Multiplex PCR System", http://www.biomerieux-diagnostics.com/filmarray-multiplex-per-system, 2014, 11 pages.

Google, "LAMP Assay Veratile Analysis", http://lava-dna.googlecode.com, 2017, 1 page.

Phillippy, Adam M. et al., "Insignia: A DNA Signature Search Web Server for Diagnostic Assay Development", Nucleic Acids Research, vol. 37, Web Server Issue, 2009, pp. W 229-W234.

Primer Explorer, "PrimerExplorer V4 Software", http://primerexplorer.jp/elamp4.0.0/index.html, 2005, 1 page.

Satya, Ravi Vijaya et al., "A High-Throughput Pipeline for the Design of Real-Time PCR Signatures", Biomed Central Ltd., BMC Bioinformatics, vol. 11, No. 340, 2010, pp. 1-10.

Van Oort, P.M. et al., "BreathDx-Molecular Analysis of Exhaled Breath as a Diagnostic Test for Ventilator-Associated Pneumonia: Protocol for a European Multicentre Observational Study", BMC Pulm Med, vol. 17, No. 1, 2017, pp. 1-8.

Genengnews, "WaferGen Launches Gene-Expression Profiling Service", Nov. 19, 2009, 1 page.

Molecular Probes, "SYTO® Orange Fluorescent Nucleic Acid Stains", Jan. 2001, 2 pages.

science lab.com Chemicals & Laboratory Equipment, "Eriochrome black T MSDS", May 21, 2013, 5 pages.

Ahmad, Farhan et al., "A CCD-Based Fluorescence Imaging System for Real-Time-Loop-Mediated Isothermal Amplification-Based Rapid and Sensitive Detection of Waterborne Pathogens on Microchips", Biomed Microdevices, vol. 13, 2011, pp. 929-937.

Ahmad, Farhan, "Rapid Detection of Pathogens and Their Antibiotic Susceptibility Using Simple Microfluidics and CCD Imaging", A Dissertation, Submitted to Michigan State University, 2011, pp. 1-188.

Altschul, Stephen F. et al., "Basic Local Alignment Search Tool", J. Mol. Biol., vol. 215, 1990, pp. 403-410.

Angus, Derek C. et al., "Epidemiology of Severe Sepsis in the United States: Analysis of Incidence, Outcome, and Associated Costs of Care", Crit. Care Med., vol. 29, No. 7, 2001, pp. 1303-1310.

Avolio, Manuela et al., "Molecular Identification of Bloodstream Pathogens in Patients Presenting to the Emergency Department with Suspected Sepsis", Shock, vol. 34, No. 1, 2010, pp. 27-30.

Baik, M., "Gene Expression Profiling of Liver and Mammary Tissues of Lactating Dairy Cows", Asian-Aust. J. Anim. Sci., vol. 22, No. 6, Jun. 2009, pp. 871-884.

Beaber, John W., "SOS Response Promotes Horizontal Dissemination of Antibiotic Resistance Genes", Nature, vol. 427, Jan. 2004, pp. 72-74.

Bergholz, Peter W. et al., "Psycrhobacter Arcticus 273-4 Uses Resource Efficiency and Molecular Motion Adaptations for Subzero Temperature Growth", Journal of Bacteriology, Apr. 2009, pp. 2340-2352.

Bone, Roger C. et al., "Definitions for Sepsis and Organ Failure and Guidelines for the Use of Innovative Therapies in Sepsis", accp/sccm Consensus Conference, vol. 101, No. 6, Jun. 1992, pp. 1644-1655.

Calandra, MD, PhD, Thierry et al., "The International Sepsis Forum Consensus Conference on Definitions of Infection in the Intensive Care Unit", Crit. Care Med.. vol. 33, No. 7, 2005, pp. 1538-1548.

Center for Disease Control, "Sepsis", Webpage last reviewed Sep. 16, 2016, pp. 1-7.

Chain, Patrick S.G. et al., "Burkholderia Xenovorans LB400 Harbors a Multi-Replicon, 913-MBP Genome Shaped for Versatility", PNAS, vol. 13, No. 42, pp. 15280-15287, (2006).

Cheng, Suzanne et al., "Effective Amplification of Long Targets from Cloned Inserts and Humon Genomic DNA", Proc. Natl. Acad. Sci. USA, vol. 91, Jun. 1994, pp. 5695-5699.

Chou, Quin et al., "Prevention of Pre-PCR Mis-Priming and Primer Dimerization Improves Low-Copy-Number Amplifications," Nucleic Acids Research, vol. 20, No. 7, 1992, pp. 1717-1723.

Cline, Janice et al., "PCR Fidelity of Pfu DNA Polymerase and Other Thermostable DNA Polymerases", Nucleic Acids Research, vol. 24, No. 18, 1996, pp. 3546-3551.

Curtis, Kelly A. et al., "Rapid Detection of HIV-1 by Reverse-Transcription, Loop-Mediated Isothermal Amplification (RT-LAMP)", Journal of Virological Methods, vol. 151, 2008, pp. 264-270.

David, Fabrice et al., "Une Methode d'Amplification Genique Isotherme—An Isothermal Gene Amplification Method", C.R. Acad. Sci. Paris, Sciences de la vie—Life Sciences, vol. 321, 1998, pp. 909-914, including an English language Abstract.

David, Fabrice, "Utiliser Proprietes Topologiques de l'ADN: Une Nouvelle Arme Contre Les Agents Pathogenes", Sep. 2002, and partial English language translation, 9 pages.

De Wilde, Bram et al., "Target Enrichment Using Parallel Nanoliter Quantitative PCR Amplification", BMC Genomics, vol. 15, No. 184, pp. 1-14, (2014).

Denef, V.J. et al., "Bipheny and Benzoate Metabolism in a Genomic Context: Outlining Genome-Wide Metabolic Networks in Burkholderia Xenovorans LB400", Applied and Environmental Microbiology, Aug. 2004, pp. 4961-4970.

Dhawan, Alok et al., "Stable Colloidal Dispersions of C60 Fullerenes in Water: Evidence for Genotoxicity", Environ. Sci. Technol., vol. 40, 2006, pp. 7394-7401.

Diem, Konrad (edited by), "Geigy Scientific Tables", Sixth Editiion, 1962, pp. 551-555.

Don, R.H. et al., "'Touchdown' PCR to Circumvent Spurious Priming During Gene Amplification", Nucleic Acids Research, vol. 19, No. 14, p. 4008, (1991).

Dugan, Lawrence et al., "Detection of Bacillus Anthracis from Spores and Cells by Loop-Mediated Isothermal Amplification Without Sample Preparation", Journal of Microbiological Methods, vol. 90, 2012, pp. 280-284.

Ethechebarne, B.E. et al., "Design of Bovine Metabolism Oligonucleotide Gene Array", Journal of Animal and Feed Sciences, vol. 13, Suppl. 1, 2004, pp. 385-388.

Fernandez, Ana S. et al., "Flexible Community Structure Correlates with Stable Community Function in Methanogenic Bioreactor Communities Perturbed by Glucose", Applied and Environmental Microbiology, Sep. 2000, pp. 4058-4067.

Geojith G. et al., "Efficacy of Loop Mediated Isothermal Amplification (LAMP) Assay fo the Laboratory Identification of *Mycobacterium turberculosis* Isolates in a Resource Limited Setting",Journal of Microbiological Methods, vol. 84, 2011, pp. 71-73.

Giegy Pharmaceuticals, "Scientific Tables", Sixth Edition, Blood—Blood Volume, 1962, pp. 65-66.

Hall, Margaret, et al., National Center for Health Statistics, "Data Briefs—Inpatient Care for Septicemia or Sepsis: A Challenge for Patients and Hospitals", No. 62, Jun. 2011, pp. 1-8.

Hashsham, Syed A. et al., "Microfluidic Systems Being Adapted for Microbial, Molecular Biological Analyses", Microbe, vol. 2, No. 11, Nov. 11, 2007, pp. 531-536.

Hashsham, Syed A. et al., "Parallel Processing of Substrate Correlates with Greater Functional Stability in Methagenic Bioreactor Communities Perturbed by Glucose", Applied and Environmental Microbiology, Sep. 2000, pp. 4050-4057.

Hayden, Matthew et al., "Multiplex-Ready PCR: a New Method for Multiplexed SSR and SNP Genotyping", BMC Genomics, Feb. 18, 2008, pp. 1-12.

Herman, James G. et al., "Methylation-Specific PCR: A Novel PCR Assay for Methylation Status of CpG Islands", Proc. Natl. Acad. Sci. USA, vol. 93, Sep. 1996, pp. 9821-9826.

(56) References Cited

OTHER PUBLICATIONS

Human Microbiome Project Consortium, "Structure, Function and Diversity of the Healthy Human Microbome", Macmillan Publishers, NATURE, vol. 486, Jun. 14, 2012, pp. 207-214.
Innis, Michael A. et al., "DNA Sequencing with Thermus Acquaticus DNA Polymerase and Direct Sequencing of Polymerase Chain Reactioin-Amplified DNA", Proc. Natl. Acad. Sci. USA, vol. 85, Dec. 1988, pp. 9436-9440.
Iwai, Shoko et al., "Gene-Targeted-Metagenomics Reveals Extensive Diversity of Aromatic Dioxygenase Genes in the Environment", The ISME Journal, vol. 4, 2010, pp. 279-285.
Jevtusevskaja, Jekaterina et al., "Combination with Antimicrobial Peptide Lyses Improves Loop-Mediated Isothermal Amplification Based Method for Chlamydia Trachomatis Detection Directly in Urine Sample", BMC Infectious Diseases, vol. 16, No. 329, 2016, pp. 1-8.
Johansson, Karin et al., "Clostridium Difficile Infection Diagnostics—Evaluation of the C. DIFF Quik Chek Complete Assay, A Rapid Enzyme Immuoassay for Detection of Toxigenic C. Difficile in Clinical Stool Samples", APMIS, vol. 124, 2016, pp. 1016-1020.
Johnston, Amy N.B. et al., "Effect of Immediate Administration of Antibiotices in Patients with Sepsis in Tertiary Care: A Systematic Review and Meta-Analysis" Cilinical Therapeutics, vol. 39, No. 1, 2017, pp. 190-202e6.
Kermekchiev, Milko B. et al., "Mutants of Taq DNA Polymerase Resistant to PCR Inhibitors Allow DNA Amplification from Whole Blood and Crude Oil Samples", Nucleic Acids Research, vol. 37, No. 5, 2009, pp. 1-14.
Kimura, Yasumasa et al., "Optimization of Turn-Back Primers in Isothermal Amplification" Nucleic Acids Research, vol. 39, No. 9, 2011, pp. 1-8.
Konstantinidis, Konstantinos T. et al., "Comparative Systems Biology Across an Evolutionary Gradient within the *Shewanella* Genus", PNAS, vol. 106, No. 37, Sep. 15, 2009, pp. 15909-15914.
Konstantinidis, Konstantinos T. et al., "Genomic Insights that Advance the Species Definition for Prokaryotes", PNAS, vol. 102, No. 7, Feb. 15, 2005, pp. 2567-2572.
Konstantinidis, Konstantinos T. et al., "Towards a Genome-Based Taxonomy for Prokaryotes", Journal of Bacteriology, Sep. 2005, pp. 6258-6264.
Kung, Ph.D., Hsiang-Ching et al., "Deaths: Final Data for 2005", National Vital Statistics Reports, CDC, vol. 56, No. 10, Apr. 24, 2008, pp. 1-121.
Li, Dong et al., "Antibiotic-Resistance Profile in Environmental Bacteria Isolated from Penicillin Production Wastewater Treatment Plant and Receiving River", Environmental Microbiology, vol. 11, No. 6, 2009, pp. 1506-1517.
Liesenfeld, O. et al., "Molecular Diagnosis of Sepsis: New Aspects and Recent Developments", European Journal of Microbiology and Immunology, vol. 4, No. 1, 2014, pp. 1-25.
Liu, Bo et al., "ARDB—Antibiotic Resistance Genes Database", Nucleic Acids Research, vol. 37, 2009, pp. D443-D447.
Liu, Yao-Guang et al., "Thermal Asymmetric Interlaced PCR: Automatable Amplification and Sequencing of Insert End Fragments from P1 and YAC Clones for Chromosome Walking" Genomics, vol. 25, 1995, pp. 674-681.
Loo, J.F.C. et al., "Sample-To-Answer on Molecular Diagnosis of Bacterial Infection Using Integrated Lab-On-A-Disc", Biosensors and Bioelectronics, vol. 93, 2017, pp. 212-219.

| Pathogen | Number | Relative frequency | Pathogenic Sites |
|---|---|---|---|
| Escherichia coli | 10404 | 0.202 | 1, 2, 3, 4, 6, 7, 8 |
| Coag-neg Staphylococcus Sp. | 7949 | 0.154 | 1, 2, 3 |
| Staphylococcus aureus | 3315 | 0.064 | 1, 2, 3, 5, 6, 7, 8, 9 |
| Enterococcus spp. | 2962 | 0.057 | 1, 2, 6 |
| Group B Beta Strep (S. agalactiae) | 2830 | 0.055 | 1, 3, 4, 5, 7 |
| Corynebacterium sp | 2787 | 0.054 | 1, 2, 3, 7 |
| Methicillin-resistant S. aureus | 2779 | 0.054 | 1, 2, 3 |
| Viridans streptococcus group | 2115 | 0.041 | 1, 3 |
| Klebsiella pneumoniae | 1934 | 0.038 | 1, 2, 3, 4, 6, 7 |
| Candida albicans | 1421 | 0.028 | 1, 3, 5, 7 |
| Group A Strep | 1184 | 0.023 | 1, 2, 3, 5, 7, 9 |
| Proteus mirabilis | 925 | 0.018 | 1, 2, 3, 7 |
| Peptostreptococcus group | 895 | 0.017 | 1, 2, 3, 4, 5, 8, 9 |
| Respiratory syncitial virus | 571 | 0.011 | 7 |
| Yeast | 528 | 0.010 | 1, 2 |
| Coliform | 511 | 0.010 | 1, 2 |
| Strep pyogenes | 500 | 0.010 | 1, 2, 3, 5, 7, 9 |
| C. difficile toxin gene | 500 | 0.010 | 6 |
| Enterobacter cloacae | 444 | 0.009 | 1, 3, 4, 6 |
| Gardnerella vaginalis | 388 | 0.008 | 5 |
| Klebsiella oxytoca | 386 | 0.007 | 1, 2, 3, 4, 6, 7 |
| Haemophilus influenzae | 329 | 0.006 | 3, 4, 7, 9 |
| Streptococcus pneumoniae | 308 | 0.006 | 1, 4, 7 |
| Citrobacter freundii | 305 | 0.006 | 1, 2, 4 |
| Ureaplasma urealyticum | 298 | 0.006 | 2, 4, 5, 7, |
| VRE faecium | 296 | 0.006 | 1, 2, 3, 4, 6 |
| Blastocystis hominis | 289 | 0.006 | 6 |
| Bacteroides fragilis | 283 | 0.005 | 1, 3, 5, 6, 7, 8 |
| Group C/G Strep | 282 | 0.005 | 1, 3, 7, 9 |
| Candida glabrata | 271 | 0.005 | 2 |
| Staph saprophyticus | 266 | 0.005 | 2 |
| Micrococcus sp | 260 | 0.005 | 1, 4, 7, 9 |
| Enterocbacter aerogenes | 258 | 0.005 | 2 |
| Bacteroides sp | 255 | 0.005 | 1, 3, 5, 7, 8 |
| Lactobacillus | 240 | 0.005 | 2 |
| Serratia marcescens | 225 | 0.004 | 1, 2, 3, 7 |
| Influenza A | 192 | 0.004 | 7 |
| Beta strep non-group A | 174 | 0.003 | 1, 2 |
| Endolimax nana | 161 | 0.003 | 6 |
| Gram negative rod | 154 | 0.003 | 1, 2, 3 |
| Morganella morganii | 154 | 0.003 | 1, 3, 7 |
| Prevotella sp | 152 | 0.003 | 1, 2, 3, 7 |
| Non-enteric Gram neg rod | 152 | 0.003 | 1, 2, 3 |
| Stenotrophomonas (x.) maltophilia | 147 | 0.003 | 1, 2, 7 |
| Moraxella catarrhalis | 141 | 0.003 | 1, 2, 3, 4, 7, 9 |
| Citrobacter koseri (diversus) | 136 | 0.003 | 1, 2, 4 |
| Staph lugdunensis | 134 | 0.003 | 1, 9 |
| Rotavirus antigen | 133 | 0.003 | 6 |
| Giardia lamblia | 121 | 0.002 | 6 |
| Anaerobic Gram neg rod | 119 | 0.002 | 1, 2 |

1 – Blood
2 – Urine
3 – Wound
4 – CNS
5 – Repro
6 – Stool
7 – Respiratory
8 – Pentoneum
9 – Bone and joints

FIG. 3

PATHOGENS WITH EXAMPLE LAMP PRIMER SEQUENCES

| | *E. coli* | | |
|---|---|---|---|
| Seq ID No: 1 | stx2 | F3 | GAGATATCGACCCCTCTTG |
| Seq ID No: 2 | | B3 | AATCTGAAAAACGGTAGAAAGT |
| Seq ID No: 3 | | FIP | TCCACAGCAAAATAACTGCCCAACATATATCTCAGGGGACCA |
| Seq ID No: 4 | | BIP | GATGTCTATCAGGCGCGTTTGCCGTATTAACGAACCCGG |
| Seq ID No: 5 | | LF | TGTGGTTAATAACAGACACCGATG |
| Seq ID No: 6 | | LB | ACCATCTTCGTCTGATTATTGAGC |
| Seq ID No: 7 | uidA | F3 | TATCTACCGCTCGCGTCG |
| Seq ID No: 8 | | B3 | CGAGCATCTCTTCAGCGT |
| Seq ID No: 9 | | FIP | TCCTTTGCCCGAATCGCATCTTAGTGAAGGCGAACAGTTCC |
| Seq ID No: 10 | | BIP | TCGATAACGTGCTGATGGTGCATGCGAGTCGGTAGGGTTG |
| Seq ID No: 11 | | LF | CGTAAAGTAGAACGGTTTGTGGTTA |
| Seq ID No: 12 | | LB | CACGCATAATGGACTGGATTGG |
| | *S. aureus* | | |
| Seq ID No: 13 | coa | F3 | GATGCTGGTACAGGTATYC |
| Seq ID No: 14 | | B3 | TTTGCATGTGTTGTTACGT |
| Seq ID No: 15 | | FIP | GCRTTTGTTTCTGATGGCTTATTGAGTGAATACAACGATGGAACAT |
| Seq ID No: 16 | | BIP | TAACGACAAATCAAGATGGCACAGCATTTGTTTTGCTTGGTTTG |
| Seq ID No: 17 | | LF | TCTTGGTCTCGCTTCATATCCAA |
| Seq ID No: 18 | | LB | GTAWCATATGGCGCTCGCCCAA |
| Seq ID No: 19 | nuc | F3 | AACAGTATATAGTGCAACTTCAA |
| Seq ID No: 20 | | B3 | CTTTGTCAAACTCGACTTCAA |
| Seq ID No: 21 | | FIP | ATGTCATTGGTTGACCTTTGTACATAAATTACATAAAGAACCTGCGA |
| Seq ID No: 22 | | BIP | TATTGGTKGATACACCTGAAACAAAATTTTTTCGTAAATGCACTTGC |
| Seq ID No: 23 | | LF | ATTTAACCGTATCACCATCAATCGC |
| Seq ID No: 24 | | LB | AGGTGTAGAGAAATATGGTCCTGAA |
| Seq ID No: 25 | mecA | F3 | ATCTCATATGCTGTTCCTGTA |
| Seq ID No: 26 | | B3 | AAAAAACGAGTAGATGCTCAA |
| Seq ID No: 27 | | FIP | AATGCAGAAAGACCAAAGCATACATGCCAATTCCACATTGTTTCG |
| Seq ID No: 28 | | BIP | TGACGCTATGATCCCAATCTAACTACTACGGTAACATTGATCGC |
| Seq ID No: 29 | | LF | TTTAAAAATCAGAACGTGGTAAAATTTTAGAC |
| Seq ID No: 30 | | LB | CCACATACCATCTTCTTTAACAAAATTAAATTG |
| | *Streptococcus spp* | | |
| Seq ID No: 31 | cfb | F3 | TGTATAGATTGTAGCTCTATCAGTT |
| Seq ID No: 32 | | B3 | AAGCCTTAACAGATGTGATTG |
| Seq ID No: 33 | | FIP | TCCATTTGCTTCAGTTGATTCAATCAGGATAAGTTAAAACCTTTTGTTC |
| Seq ID No: 34 | | BIP | TGCGAATAACCAGCTTAGTTATCCCACTTTTTCAACTCAACATTTAGC |
| Seq ID No: 35 | | LF | GCTCAAGTTAACGATGTAAAGGCATTA |
| Seq ID No: 36 | | LB | TCCCATATCAATATTTGCTTGACTAACC |
| Seq ID No: 37 | mstA | F3 | GCTGATGTGATTTTCTATAATGGTA |
| Seq ID No: 38 | | B3 | CAATCAATTGTTTGGCAATGT |
| Seq ID No: 39 | | FIP | ACGGCAAAGTAATCTTTGTTTTTCGCAATCTAGAAGATGGTGGGC |
| Seq ID No: 40 | | BIP | ACTTGGAAGGTGCAAGCGAAAAATGATTCCGTTTTCGAGAT |
| Seq ID No: 41 | | LF | GCATTTTTCACTAGTTTGGTGAACC |
| Seq ID No: 42 | | LB | GAAAAGAAGATCCACATGCTTGGT |
| Seq ID No: 43 | scpA | F3 | CACACGTGTCAGGGATCT |
| Seq ID No: 44 | | B3 | CCTTAGCTCCCAAGTTGAC |
| Seq ID No: 45 | | FIP | TCAGGCATCGCACCTTCTAGTGTCAGGAAATGCTCCAT |
| Seq ID No: 46 | | BIP | TCAATTGCTTTTGATGCGTGTCTCTCTGATAGCTTGAGCGTA |
| Seq ID No: 47 | | LF | GCGGTAAGGTTCTTTCGTTTCAG |
| Seq ID No: 48 | | LB | AATGGACTAGCAGACTATGCTCGTA |
| Seq ID No: 49 | lmb | F3 | CACAAGGCATTGACCCTG |
| Seq ID No: 50 | | B3 | GCACCTTTTTAAATTTTTGAGTG |
| Seq ID No: 51 | | FIP | AGCTCTTTAGCGATATTAACAGCTTTTTATGACCCACATACCTGG |
| Seq ID No: 52 | | BIP | AGGACGTTTGGATCCTAAACACAATCTTCAGTTAGTTGCTCTGC |
| Seq ID No: 53 | | LF | CCAGCTAAAACGGGATCCGT |
| Seq ID No: 54 | | LB | ACAGTTACACTAAAAAGGCTAAGGC |

FIG 4

| Microbial species | Hospital Culture Sensitivities | | OpenArray Gene detection | | % of Resistance Undetected | % of Sensitivity Detected |
| --- | --- | --- | --- | --- | --- | --- |
| | Antibiotic resistance count | Antibiotic sensitive count | Antibiotic resistance over-call | Antibiotic resistance under-call | | |
| *Corynebacterium* spp | 3 | 3 | 0 | 2 | 66.67 | 100 |
| *Staphylococcus aureus* | 5 | 16 | 0 | 1 | 20.00 | 100 |
| Methicillin-resistant *Staph. aureus* | 14 | 10 | 0 | 1 | 7.14 | 100 |
| *Staphylococcus epidermidis* | 13 | 8 | 0 | 2 | 15.38 | 100 |
| *Streptococcus pyogenes* | 1 | 13 | 0 | 1 | 100.00 | 100 |
| *Streptococcus agalactiae* | 1 | 12 | 0 | 0 | 0.00 | 100 |
| *Proteus mirabilis* | 2 | 15 | 0 | 2 | 100.00 | 100 |
| *Eschericia coli* | 3 | 17 | 0 | 0 | 0.00 | 100 |
| *Klebsiella pneumoniae* | 1 | 19 | 0 | 0 | 0.00 | 100 |
| *Enterococcus faecalis* | 9 | 11 | 0 | 3 | 33.33 | 100 |
| Total | | | 0 | 12 | 34.25 | 100 |

FIG. 5

```
                            SEQUENCE LISTING

<160> NUMBER OF SEQ ID NOS: 54

<210> SEQ ID NO 1
<211> LENGTH: 19
<212> TYPE: DNA
<213> ORGANISM: Escherichia coli
<220> FEATURE:
<221> NAME/KEY: primer_bind
<222> LOCATION: (1)..(19)

<400> SEQUENCE: 1
gagatatcga cccctcttg                                                   19

<210> SEQ ID NO 2
<211> LENGTH: 22
<212> TYPE: DNA
<213> ORGANISM: Escherichia coli
<220> FEATURE:
<221> NAME/KEY: primer_bind
<222> LOCATION: (1)..(22)

<400> SEQUENCE: 2
aatctgaaaa acggtagaaa gt                                               22

<210> SEQ ID NO 3
<211> LENGTH: 42
<212> TYPE: DNA
<213> ORGANISM: Escherichia coli
<220> FEATURE:
<221> NAME/KEY: primer_bind
<222> LOCATION: (1)..(42)

<400> SEQUENCE: 3
tccacagcaa ataactgcc caacatatat ctcaggggac ca                          42

<210> SEQ ID NO 4
<211> LENGTH: 40
<212> TYPE: DNA
<213> ORGANISM: Escherichia coli
<220> FEATURE:
<221> NAME/KEY: primer_bind
<222> LOCATION: (1)..(40)

<400> SEQUENCE: 4
gatgtctatc aggcgcgttt tgccgtatta acgaacccgg                            40

<210> SEQ ID NO 5
<211> LENGTH: 24
<212> TYPE: DNA
<213> ORGANISM: Escherichia coli
<220> FEATURE:
<221> NAME/KEY: primer_bind
<222> LOCATION: (1)..(24)

<400> SEQUENCE: 5
tgtggttaat aacagacacc gatg                                             24

<210> SEQ ID NO 6
<211> LENGTH: 24
<212> TYPE: DNA
<213> ORGANISM: Escherichia coli
<220> FEATURE:
<221> NAME/KEY: primer_bind
```

```
<222> LOCATION: (1)..(24)

<400> SEQUENCE: 6
accatcttcg tctgattatt gagc                                          24

<210> SEQ ID NO 7
<211> LENGTH: 18
<212> TYPE: DNA
<213> ORGANISM: Escherichia coli
<220> FEATURE:
<221> NAME/KEY: primer_bind
<222> LOCATION: (1)..(18)

<400> SEQUENCE: 7
tatctaccgc tcgcgtcg                                                 18

<210> SEQ ID NO 8
<211> LENGTH: 18
<212> TYPE: DNA
<213> ORGANISM: Escherichia coli
<220> FEATURE:
<221> NAME/KEY: primer_bind
<222> LOCATION: (1)..(18)

<400> SEQUENCE: 8
cgagcatctc ttcagcgt                                                 18

<210> SEQ ID NO 9
<211> LENGTH: 41
<212> TYPE: DNA
<213> ORGANISM: Escherichia coli
<220> FEATURE:
<221> NAME/KEY: primer_bind
<222> LOCATION: (1)..(41)

<400> SEQUENCE: 9
tcctttgccc gaatcgcatc ttagtgaagg cgaacagttc c                       41

<210> SEQ ID NO 10
<211> LENGTH: 40
<212> TYPE: DNA
<213> ORGANISM: Escherichia coli
<220> FEATURE:
<221> NAME/KEY: primer_bind
<222> LOCATION: (1)..(40)

<400> SEQUENCE: 10
tcgataacgt gctgatggtg catgcgagtc ggtagggttg                         40

<210> SEQ ID NO 11
<211> LENGTH: 25
<212> TYPE: DNA
<213> ORGANISM: Escherichia coli
<220> FEATURE:
<221> NAME/KEY: primer_bind
<222> LOCATION: (1)..(25)

<400> SEQUENCE: 11
cgtaaagtag aacggtttgt ggtta                                         25

<210> SEQ ID NO 12
<211> LENGTH: 22
<212> TYPE: DNA
<213> ORGANISM: Escherichia coli
<220> FEATURE:
<221> NAME/KEY: primer_bind
<222> LOCATION: (1)..(22)
```

<400> SEQUENCE: 12
cacgcataat ggactggatt gg                                                    22

<210> SEQ ID NO 13
<211> LENGTH: 19
<212> TYPE: DNA
<213> ORGANISM: Staphylococcus aureus
<220> FEATURE:
<221> NAME/KEY: primer_bind
<222> LOCATION: (1)..(19)

<400> SEQUENCE: 13
gatgctggta caggtatyc                                                        19

<210> SEQ ID NO 14
<211> LENGTH: 19
<212> TYPE: DNA
<213> ORGANISM: Staphylococcus aureus
<220> FEATURE:
<221> NAME/KEY: primer_bind
<222> LOCATION: (1)..(19)

<400> SEQUENCE: 14
tttgcatgtg ttgttacgt                                                        19

<210> SEQ ID NO 15
<211> LENGTH: 46
<212> TYPE: DNA
<213> ORGANISM: Staphylococcus aureus
<220> FEATURE:
<221> NAME/KEY: primer_bind
<222> LOCATION: (1)..(46)

<400> SEQUENCE: 15
gcrtttgttt ctgatggctt attgagtgaa tacaacgatg gaacat                          46

<210> SEQ ID NO 16
<211> LENGTH: 44
<212> TYPE: DNA
<213> ORGANISM: Staphylococcus aureus
<220> FEATURE:
<221> NAME/KEY: primer_bind
<222> LOCATION: (1)..(44)

<400> SEQUENCE: 16
taacgacaaa tcaagatggc acagcatttg ttttgcttgg tttg                            44

<210> SEQ ID NO 17
<211> LENGTH: 23
<212> TYPE: DNA
<213> ORGANISM: Staphylococcus aureus
<220> FEATURE:
<221> NAME/KEY: primer_bind
<222> LOCATION: (1)..(23)

<400> SEQUENCE: 17
tcttggtctc gcttcatatc caa                                                   23

<210> SEQ ID NO 18
<211> LENGTH: 22
<212> TYPE: DNA
<213> ORGANISM: Staphylococcus aureus
<220> FEATURE:
<221> NAME/KEY: primer_bind
<222> LOCATION: (1)..(22)

<400> SEQUENCE: 18
gtawcatatg gcgctcgccc aa                                    22

<210> SEQ ID NO 19
<211> LENGTH: 23
<212> TYPE: DNA
<213> ORGANISM: Staphylococcus aureus
<220> FEATURE:
<221> NAME/KEY: primer_bind
<222> LOCATION: (1)..(23)

<400> SEQUENCE: 19
aacagtatat agtgcaactt caa                                   23

<210> SEQ ID NO 20
<211> LENGTH: 21
<212> TYPE: DNA
<213> ORGANISM: Staphylococcus aureus
<220> FEATURE:
<221> NAME/KEY: primer_bind
<222> LOCATION: (1)..(21)

<400> SEQUENCE: 20
ctttgtcaaa ctcgacttca a                                     21

<210> SEQ ID NO 21
<211> LENGTH: 47
<212> TYPE: DNA
<213> ORGANISM: Staphylococcus aureus
<220> FEATURE:
<221> NAME/KEY: primer_bind
<222> LOCATION: (1)..(47)

<400> SEQUENCE: 21
atgtcattgg ttgacctttg tacataaatt acataaagaa cctgcga         47

<210> SEQ ID NO 22
<211> LENGTH: 48
<212> TYPE: DNA
<213> ORGANISM: Staphylococcus aureus
<220> FEATURE:
<221> NAME/KEY: primer_bind
<222> LOCATION: (1)..(48)

<400> SEQUENCE: 22
tattggtkga tacacctgaa acaaaatttt tttcgtaaat gcacttgc        48

<210> SEQ ID NO 23
<211> LENGTH: 25
<212> TYPE: DNA
<213> ORGANISM: Staphylococcus aureus
<220> FEATURE:
<221> NAME/KEY: primer_bind
<222> LOCATION: (1)..(25)

<400> SEQUENCE: 23
atttaaccgt atcaccatca atcgc                                 25

<210> SEQ ID NO 24
<211> LENGTH: 25
<212> TYPE: DNA
<213> ORGANISM: Staphylococcus aureus
<220> FEATURE:
<221> NAME/KEY: primer_bind
<222> LOCATION: (1)..(25)

<400> SEQUENCE: 24
aggtgtagag aaatatggtc ctgaa                                              25

<210> SEQ ID NO 25
<211> LENGTH: 21
<212> TYPE: DNA
<213> ORGANISM: Staphylococcus aureus
<220> FEATURE:
<221> NAME/KEY: primer_bind
<222> LOCATION: (1)..(21)

<400> SEQUENCE: 25
atctcatatg ctgttcctgt a                                                  21

<210> SEQ ID NO 26
<211> LENGTH: 21
<212> TYPE: DNA
<213> ORGANISM: Staphylococcus aureus
<220> FEATURE:
<221> NAME/KEY: primer_bind
<222> LOCATION: (1)..(21)

<400> SEQUENCE: 26
aaaaaacgag tagatgctca a                                                  21

<210> SEQ ID NO 27
<211> LENGTH: 45
<212> TYPE: DNA
<213> ORGANISM: Staphylococcus aureus
<220> FEATURE:
<221> NAME/KEY: primer_bind
<222> LOCATION: (1)..(45)

<400> SEQUENCE: 27
aatgcagaaa gaccaaagca tacatgccaa ttccacattg tttcg                         45

<210> SEQ ID NO 28
<211> LENGTH: 44
<212> TYPE: DNA
<213> ORGANISM: Staphylococcus aureus
<220> FEATURE:
<221> NAME/KEY: primer_bind
<222> LOCATION: (1)..(44)

<400> SEQUENCE: 28
tgacgctatg atcccaatct aactactacg gtaacattga tcgc                          44

<210> SEQ ID NO 29
<211> LENGTH: 31
<212> TYPE: DNA
<213> ORGANISM: Staphylococcus aureus
<220> FEATURE:
<221> NAME/KEY: primer_bind
<222> LOCATION: (1)..(31)

<400> SEQUENCE: 29
tttaaaatca gaacgtggta aaattttaga c                                       31

<210> SEQ ID NO 30
<211> LENGTH: 33
<212> TYPE: DNA
<213> ORGANISM: Staphylococcus aureus
<220> FEATURE:
<221> NAME/KEY: primer_bind
<222> LOCATION: (1)..(33)

<400> SEQUENCE: 30

-continued

```
ccacatacca tcttctttaa caaaattaaa ttg                          33

<210> SEQ ID NO 31
<211> LENGTH: 25
<212> TYPE: DNA
<213> ORGANISM: Streptococcus spp
<220> FEATURE:
<221> NAME/KEY: primer_bind
<222> LOCATION: (1)..(25)

<400> SEQUENCE: 31
tgtatagatt gtagctctat cagtt                                  25

<210> SEQ ID NO 32
<211> LENGTH: 21
<212> TYPE: DNA
<213> ORGANISM: Streptococcus spp
<220> FEATURE:
<221> NAME/KEY: primer_bind
<222> LOCATION: (1)..(21)

<400> SEQUENCE: 32
aagccttaac agatgtgatt g                                      21

<210> SEQ ID NO 33
<211> LENGTH: 50
<212> TYPE: DNA
<213> ORGANISM: Streptococcus spp
<220> FEATURE:
<221> NAME/KEY: primer_bind
<222> LOCATION: (1)..(50)

<400> SEQUENCE: 33
tccatttgct tcagttgatt caattcagga taagttaaaa cctttgttc         50

<210> SEQ ID NO 34
<211> LENGTH: 48
<212> TYPE: DNA
<213> ORGANISM: Streptococcus spp
<220> FEATURE:
<221> NAME/KEY: primer_bind
<222> LOCATION: (1)..(48)

<400> SEQUENCE: 34
tgcgaataac cagcttagtt atcccacttt ttcaactcaa catttagc          48

<210> SEQ ID NO 35
<211> LENGTH: 27
<212> TYPE: DNA
<213> ORGANISM: Streptococcus spp
<220> FEATURE:
<221> NAME/KEY: primer_bind
<222> LOCATION: (1)..(27)

<400> SEQUENCE: 35
gctcaagtta acgatgtaaa ggcatta                                27

<210> SEQ ID NO 36
<211> LENGTH: 28
<212> TYPE: DNA
<213> ORGANISM: Streptococcus spp
<220> FEATURE:
<221> NAME/KEY: primer_bind
<222> LOCATION: (1)..(28)

<400> SEQUENCE: 36
tcccatatca atatttgctt gactaacc                                28
```

<210> SEQ ID NO 37
<211> LENGTH: 25
<212> TYPE: DNA
<213> ORGANISM: Streptococcus spp
<220> FEATURE:
<221> NAME/KEY: primer_bind
<222> LOCATION: (1)..(25)

<400> SEQUENCE: 37
gctgatgtga ttttctataa tggta                                      25

<210> SEQ ID NO 38
<211> LENGTH: 21
<212> TYPE: DNA
<213> ORGANISM: Streptococcus spp
<220> FEATURE:
<221> NAME/KEY: primer_bind
<222> LOCATION: (1)..(21)

<400> SEQUENCE: 38
caatcaattg tttggcaatg t                                          21

<210> SEQ ID NO 39
<211> LENGTH: 45
<212> TYPE: DNA
<213> ORGANISM: Streptococcus spp
<220> FEATURE:
<221> NAME/KEY: primer_bind
<222> LOCATION: (1)..(45)

<400> SEQUENCE: 39
acggcaaagt aatctttgtt tttcgcaatc tagaagatgg tgggc                45

<210> SEQ ID NO 40
<211> LENGTH: 41
<212> TYPE: DNA
<213> ORGANISM: Streptococcus spp
<220> FEATURE:
<221> NAME/KEY: primer_bind
<222> LOCATION: (1)..(41)

<400> SEQUENCE: 40
acttggaagg tgcaagcgaa aaatgattcc gttttcgaga t                    41

<210> SEQ ID NO 41
<211> LENGTH: 25
<212> TYPE: DNA
<213> ORGANISM: Streptococcus spp
<220> FEATURE:
<221> NAME/KEY: primer_bind
<222> LOCATION: (1)..(25)

<400> SEQUENCE: 41 gcattttca ctagtttggt gaacc                                       25

<210> SEQ ID NO 42
<211> LENGTH: 24
<212> TYPE: DNA
<213> ORGANISM: Streptococcus spp
<220> FEATURE:
<221> NAME/KEY: primer_bind
<222> LOCATION: (1)..(24)

<400> SEQUENCE: 42
gaaaagaaga tccacatgct tggt                                       24

```
<210> SEQ ID NO 43
<211> LENGTH: 18
<212> TYPE: DNA
<213> ORGANISM: Streptococcus spp
<220> FEATURE:
<221> NAME/KEY: primer_bind
<222> LOCATION: (1)..(18)

<400> SEQUENCE: 43
cacacgtgtc agggatct                                                 18

<210> SEQ ID NO 44
<211> LENGTH: 19
<212> TYPE: DNA
<213> ORGANISM: Streptococcus spp
<220> FEATURE:
<221> NAME/KEY: primer_bind
<222> LOCATION: (1)..(19)

<400> SEQUENCE: 44
ccttagctcc caagttgac                                                19

<210> SEQ ID NO 45
<211> LENGTH: 38
<212> TYPE: DNA
<213> ORGANISM: Streptococcus spp
<220> FEATURE:
<221> NAME/KEY: primer_bind
<222> LOCATION: (1)..(38)

<400> SEQUENCE: 45
tcaggcatcg caccttctag tgtcaggaaa tgctccat                           38

<210> SEQ ID NO 46
<211> LENGTH: 42
<212> TYPE: DNA
<213> ORGANISM: Streptococcus spp
<220> FEATURE:
<221> NAME/KEY: primer_bind
<222> LOCATION: (1)..(42)

<400> SEQUENCE: 46
tcaattgctt ttgatgcgtg tctctctgat agcttgagcg ta                      42

<210> SEQ ID NO 47
<211> LENGTH: 23
<212> TYPE: DNA
<213> ORGANISM: Streptococcus spp
<220> FEATURE:
<221> NAME/KEY: primer_bind
<222> LOCATION: (1)..(23)

<400> SEQUENCE: 47
gcggtaaggt tctttcgttt cag                                           23

<210> SEQ ID NO 48
<211> LENGTH: 25
<212> TYPE: DNA
<213> ORGANISM: Streptococcus spp
<220> FEATURE:
<221> NAME/KEY: primer_bind
<222> LOCATION: (1)..(25)

<400> SEQUENCE: 48
aatggactag cagactatgc tcgta                                         25
```

```
<210> SEQ ID NO 49
<211> LENGTH: 18
<212> TYPE: DNA
<213> ORGANISM: Streptococcus spp
<220> FEATURE:
<221> NAME/KEY: primer_bind
<222> LOCATION: (1)..(18)

<400> SEQUENCE: 49
cacaaggcat tgaccctg                                                   18

<210> SEQ ID NO 50
<211> LENGTH: 23
<212> TYPE: DNA
<213> ORGANISM: Streptococcus spp
<220> FEATURE:
<221> NAME/KEY: primer_bind
<222> LOCATION: (1)..(23)

<400> SEQUENCE: 50
gcaccttttt aaatttttga gtg                                             23

<210> SEQ ID NO 51
<211> LENGTH: 45
<212> TYPE: DNA
<213> ORGANISM: Streptococcus spp
<220> FEATURE:
<221> NAME/KEY: primer_bind
<222> LOCATION: (1)..(45)

<400> SEQUENCE: 51
agctctttag cgatattaac agcttttat gacccacata cctgg                      45

<210> SEQ ID NO 52
<211> LENGTH: 44
<212> TYPE: DNA
<213> ORGANISM: Streptococcus spp
<220> FEATURE:
<221> NAME/KEY: primer_bind
<222> LOCATION: (1)..(44)

<400> SEQUENCE: 52
aggacgtttg gatcctaaac acaatcttca gttagttgct ctgc                      44

<210> SEQ ID NO 53
<211> LENGTH: 20
<212> TYPE: DNA
<213> ORGANISM: Streptococcus spp
<220> FEATURE:
<221> NAME/KEY: primer_bind
<222> LOCATION: (1)..(20)

<400> SEQUENCE: 53
ccagctaaaa cgggatccgt                                                 20

<210> SEQ ID NO 54
<211> LENGTH: 25
<212> TYPE: DNA
<213> ORGANISM: Streptococcus spp
<220> FEATURE:
<221> NAME/KEY: primer_bind
<222> LOCATION: (1)..(25)

<400> SEQUENCE: 54
acagttacac taaaaaggct aaggc                                           25
```

METHOD OF IMPROVED IDENTIFICATION OF AND ANTIBIOTIC RESISTANCE OF SEPSIS-RELATED MICROORGANISMS

CROSS REFERENCE TO RELATED APPLICATIONS

This application is a continuation of U.S. patent application Ser. No. 14/600,696, now U.S. Pat. No. 10,260,111, filed on Jan. 20, 2015, which claims the benefit of U.S. Provisional Patent Application No. 61/929,175, filed on Jan. 20, 2014, the contents of which are incorporated herein by reference.

TECHNICAL FIELD

The present disclosure relates to methods of pathogen detection and, more specifically, to particular methods of identification of pathogenic species and their antibiotic resistance in relation to treatment of sepsis.

This disclosure, in accordance with 37 C.F.R. § 1.52 incorporates by reference the sequence listing material contained within text file titled "06854400002_ST25.txt", created on May 18, 2015 and totaling 11,311 bytes.

BACKGROUND OF THE DISCLOSURE

Sepsis, an overwhelming microbial infection of the blood, is the tenth leading cause of death in the United States and is responsible for 6% of all human deaths. Sepsis represents a large and growing burden in the healthcare setting due to increased prevalence of antibiotic resistant strains.

Delivering rapid, cutting edge molecular methods at the point-of-care (POC) can greatly enhance an ability to diagnose and treat sepsis and combat the rise of multi-drug-resistant strains by precise early determination of appropriate antibiotic coverage.

Current sepsis management is severely limited by an inability to rapidly diagnose the pathogen(s) responsible for a critically ill patient's infection. When untreated, septic patients typically have hours to live. Thus, blood cultures are drawn from a patient at the time that sepsis is suspected and 3-4 broad-spectrum intravenous antibiotics are introduced to eliminate virtually all potential pathogens. Treatments are only de-escalated three to five days later as laboratory results return, indicating the pathogenic strain and its antibiotic sensitivity profile. Due to the extended length between diagnosis and de-escalation of treatment there remains opportunity for improvement.

SUMMARY OF THE DISCLOSURE

This disclosure provides an improved method for detecting whether sepsis-related microorganisms are present in a fluid sample. The method comprises the steps of: collecting the fluid sample from a patient; fractioning the fluid sample to isolate a quantity of microorganism cells; extracting a portion of the microorganism cells from the fluid sample; lysing a portion of the microorganism cells extracted from the fluid sample to extract microorganism DNA; amplifying the microorganism DNA from the microorganism cells from a predetermined set of DNA primers to determine whether sepsis-related microorganisms are present within the fluid sample.

This disclosure also provides an alternative method comprising the steps of: collecting the fluid sample from a patient; fractioning the fluid sample to isolate a quantity of microorganism cells; extracting a portion of the microorganism cells from the fluid sample; lysing a portion of the microorganism cells extracted from the fluid sample to extract microorganism DNA therefrom; purifying the microorganism DNA; precipitating the purified microorganism DNA with an antisolvent; dissolving the precipitated microorganism DNA in a buffer solution; amplifying the microorganism DNA from the microorganism cells; hybridizing the amplified microorganism DNA to a chip with a predetermined second set of genetic markers to determine antibiotic-resistance sepsis-related microorganisms are present within the sample.

BRIEF DESCRIPTION OF THE DRAWINGS

Other advantages in the present disclosure will be readily appreciated as the same becomes better understood by reference to the following detailed description when considered in connection with the accompanying drawings:

FIG. 3 is a table of the identified microorganism species and their particular genetic markers identified by the methods of FIGS. 1 and 2;

FIG. 4 is a table of pathogens with example LAMP primer sequences; and

FIG. 5 is a table of identified microorganisms and their antibiotic resistance levels as a result of the methods shown in FIGS. 1 and 2.

Corresponding reference characters indicate corresponding parts throughout the drawings.

DETAILED DESCRIPTION OF THE DISCLOSURE

A selected embodiment of the present disclosure will now be described with reference to the drawings. It will be apparent to those skilled in the art from this disclosure that the following description of the embodiments of the present disclosure is provided for illustration only and not for the purpose of limiting the disclosure as defined by the appended claims and their equivalents. Unless other noted, all percentages and ratios are by weight. All references are expressly incorporated herein by reference in various non-limiting embodiments.

Figure 1:
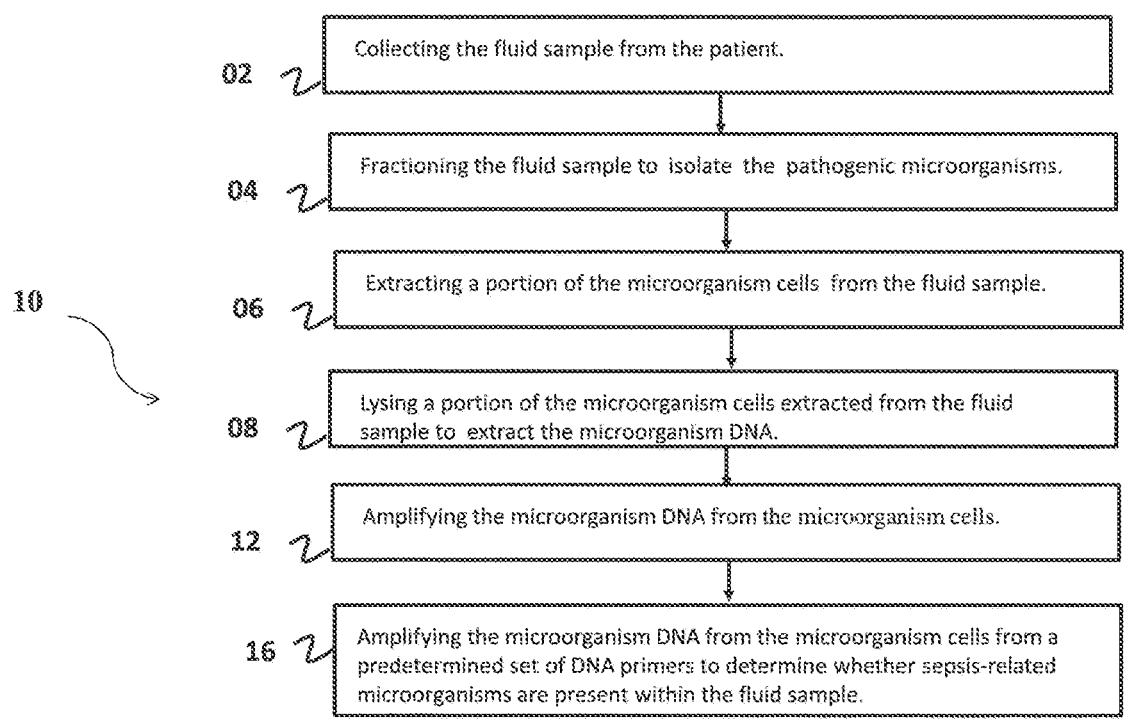
FIG. 1 is a representative flowchart of one embodiment of the method.

This disclosure provides a method 10, an example of which is set forth in FIG. 1. The method 10 detects sepsis-related microorganisms are present in a fluid sample. Currently, twenty microorganisms account for about 87% of sepsis-related microbial infections identified. Moreover, almost all known microbes that cause sepsis can be accounted for in a list of 50, as shown in FIG. 3. FIG. 4 indicates the pathogens as identified with example LAMP primer sequences.

The improved method 10 begins by collecting 02 the fluid sample from a patient. A patient may be a human that has been identified with sepsis. Other animals, such as livestock, that are also susceptible to sepsis may also be "patients" for the purposes of this disclosure. The most common fluid sample that can be used is blood (e.g. collected by way of a syringe from the patient). Typically, the sample size of blood may is from one to ten milliliters but can vary depending on the size of the patient and a person of skill in the art's decision to run additional analysis.

In another embodiment, the fluid sample may be any other bodily fluid type that could be used for identification of sepsis-related microorganisms. Fluid samples from urine, cerebral spinal fluid, stool, and/or mucous membranes (i.e. mammary milk, sputum and genitourinary swab) may be utilized in order to provide more localized analysis for sepsis-related organisms. This list of fluids is not meant to be limiting and any additional fluids and or combination of fluids (i.e. aspiration from an abscess or wound) may also be used. Greater than 1 ml may be needed from each biologic fluid type. No upper limit regarding sample size theoretically exists, though approximately 10 ml is typically used. Smaller sample volume is generally available for wound and cerebrospinal fluid samples, though absolute concentration of pathogen is increased, allowing detection with a lower sample abundance. Blood samples are typically diluted to 1-10% of reaction mixture. Urine samples are typically diluted to 10-25% of reaction mixture. Sputum samples are typically diluted to 10-25% of reaction mixture. Stool samples are typically diluted to 2-5% of total reaction mixture. Wound samples are typically diluted to 1-5% of total reaction mixture. Cerebrospinal fluid is typically diluted to 10-25% of reaction mixture.

Next, the fluid sample is fractioned 04 in order to isolate a quantity of microorganism cells. This promotes an initial concentration of cells and DNA in order to continue on with the amplification process. In one embodiment, centrifugal force is applied to the fluid sample in order to isolate the quantity of microorganisms within one of three visible fractions of the fluid sample. In another embodiment, additional filtration methods and or variations on isolating the microorganism cells are also applicable depending on the fluid sample type. An alternative method for enhanced bacterial concentration for improved detection includes use of a micropillar microfluidics peripheral filtration device. This would be expected to fractionate and concentrate microorganisms (size <3 micron diameter). Additional fractions of white blood cells, red blood cells, and plasma would be separated for possible use with other medical diagnostic tests. Next, the method 10 includes the step of extracting 06 a portion of the microorganism cells from the fractionalized fluid sample. This is to promote optimal concentration of microorganism cells and microorganism DNA for the remaining steps within the method 10. It is expected that >1 ng of DNA per reaction well is needed for reliable and accurate detection of microorganisms.

Next, the method 10 includes the step of lysing 08 a portion of the microorganism cells extracted from the fluid sample to extract the microorganism DNA therefrom. In one embodiment this involves heat lysis for 95 degrees C. for 5 minutes of the extracted portion of microorganism cells to break down cell membranes and suspend the microorganism DNA within the sample fraction. Other methods are possible (mechanical, liquid homogenization, sonication, freezer-thaw).

Next, the method 10 includes the step of amplifying 12 the microorganism DNA from the microorganism cells. In one embodiment, a polymerase chain reaction (PCR) is used in order to increase the amount of DNA within the extracted sample. For example, the industrial application of the method within this disclosure may utilize isothermal loop-mediated polymerase chain reaction (LAMP) DNA amplification to accurately identify and replicate the microorganism DNA within the fluid sample. LAMP typically proceeds by high temperature isothermal amplification of a microorganism DNA template at a target temperature of from 60 to 65° C. with two to three pairs of primers used and a polymerase enzyme with high strand displacement and replicative activity (the recombinant DNA polymerase is able to displace downstream DNA encountered during synthesis, and proceeds at a rapid rate). In one embodiment, the method 10 employs four primers targeted precisely to five to six distinct regions on the gene to maximize specificity to the sepsis-related microorganisms. In another embodiment, the method 10 employs six primers related to six distinct regions on a gene to maximize the specificity to the sepsis-related microorganism. Alternate PCR techniques may also be used in order to account for lab conditions and available timeframes in conducting the method 10.

In another embodiment of the present disclosure, the amplification of the microorganism DNA is conducted until an identifiable concentration is reached. Having an identified concentration of the microorganism DNA promotes identification of the possible microorganisms within the fluid sample. In various embodiments, approximately 0.5 ng DNA/reaction is needed for successful amplification.

The industrial application of the method 10 within this disclosure may utilize a Gene-Z POC analysis machine to return data related to the positive identification of microorganism based on amplification of microbial DNA within the fluid sample by specific primers in the Gene-Z plate reaction wells. For example, data may be delivered in the form of time to threshold and estimated copy number of microorganism nucleotide sequences based on calibration curves that have been generated by lab sample serial dilution testing. Baseline signal intensity can be generated during the first 6 minutes of an amplification run. The baseline signal can then be subtracted from raw signals and the difference curves are smoothed using average signal intensity from 20 consecutive points. Dividing the threshold difference by the maximum difference then normalizes curves. Time to threshold can then be calculated as the time to normalized difference in threshold exceeding an arbitrary cut-off of 0.1.

Finally, the method 10 includes the step of amplifying 16 the microorganism DNA by a predetermined set of DNA primers to determine whether sepsis-related microorganisms are present within the fluid sample. In one embodiment, many or all sepsis-related microorganisms can be determined based on particular primers. For example, Presence of *Staphylococcus aureus* can be detected with vicK, nuc and coA gene amplification, methicillin resistance detected by mecA amplification. *Staphylococcus epidermidis* can be identified by 16S RNA with methicillin resistance detected by mecA amplification. *Streptococcus agalactiae* species determination can be made based on ssa and mstA amplifications. *Streptococcus pyogenes* can be identified through mstA amplification. *E. coli* species can be identified based on uidA amplification and determined to be non-pathogenic (O194 strain) based on stx1, stx2 and eaeA negativity. *Klebsiella pneumoniae* can be identified by uge, wabB gene amplifications. *Enterococcus faecalis* can be identified by ef0027, and ace. In various embodiments, up to 50 sepsis-related microorganisms can have primers for testing through the methods of this disclosure. The primers are typically designed from a consensus of alleles for a gene unique to the microbial species. Primers targeting virulence and antibiotic resistance markers for bacterial pathogens can be designed using PrimerExplorer4 or retrieved from the literature. Additional methods of microbial signature identification include employment of open source resources such as the Tool for PCR Signature Identification (TOPSI) (http://www.bh-sai.org/downloads/topsi.tar.gz), the Insignia Center for Bioinformatics and Computational Biology (http://insignia.cb-cb.umd.edu). High throughput primer generation is also possible using the open-source program LAVA (LAMP Assay Veratile Analysis) (http://lava-dna.googlecode.com/). Primer specificity is specifically checked against the NCBI GeneBank database using NCBI BLAST. These primers can be supplied and PCR validation reactions performed according to standard protocols for both conventional RT-PCR thermocycler analysis and the Gene-Z device.

Antibiotic Resistance Analysis

Figure 2:
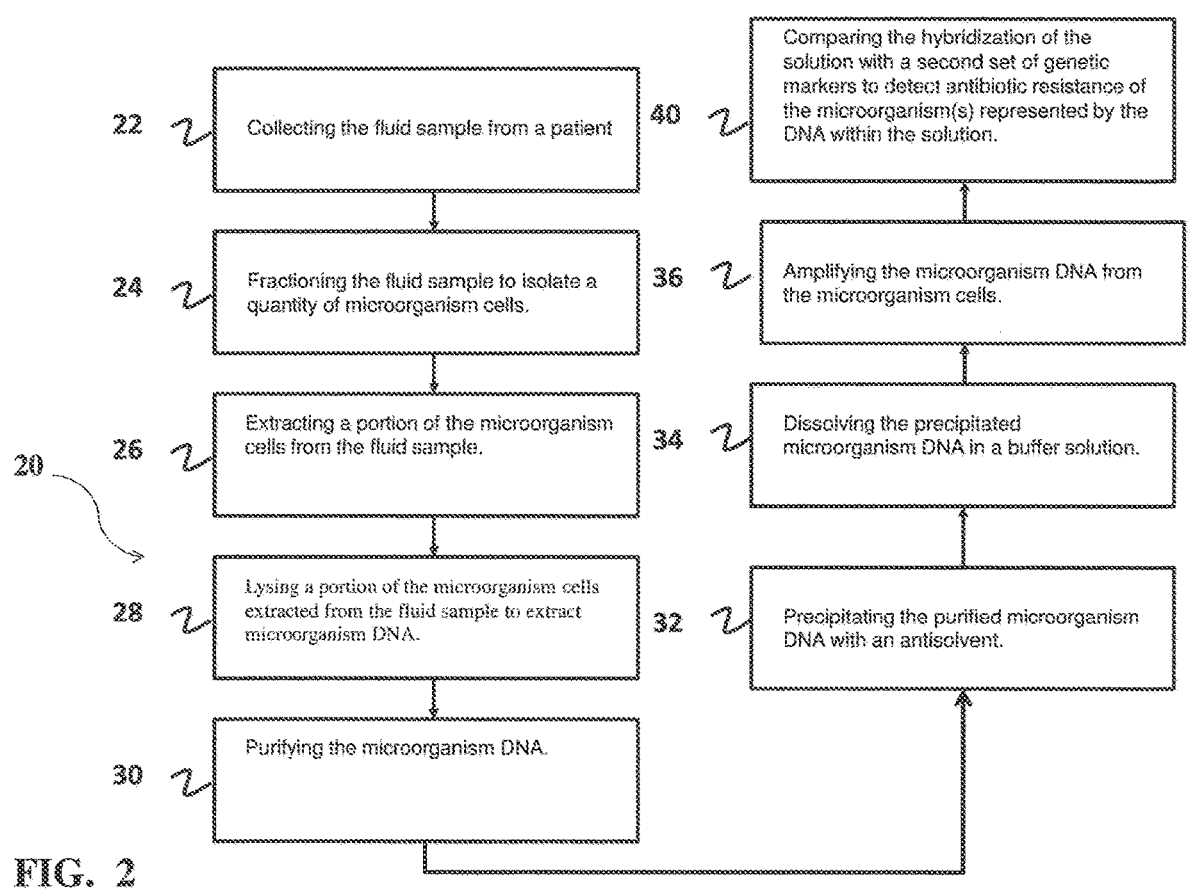
FIG. 2 is a representative flowchart of an alternate embodiment of the method.

In another embodiment of the present disclosure, e.g. as shown in FIG. 2, the disclosure describes an alternate improved method 20 for detecting whether antibiotic-resistant sepsis-related microorganisms are present in a fluid sample.

The method 20 includes the steps of collecting 22 the fluid sample from a patient (as described at step 02 above); fractioning 24 the fluid sample to isolate a quantity of microorganism cells (as described at step 04 above); extracting 26 a portion of the microorganism cells from the fluid sample (as described at step 06 above); and lysing 28 a portion of the microorganism cells extracted from the fluid sample to extract microorganism DNA (as described at step 08 above). Any one or more of these steps may be the same or different from those described above.

Then, the method 20 further includes the step of purifying 30 the microorganism DNA. In one embodiment this is done through a phenol cholorform extraction (by mixing the sample with equal volumes of a phenol chloroform mixture), in order to concentrate the nucleic acids and reduce the presence of proteins attached to the microorganism DNA from the fluid solution.

Next, the method 20 includes the step of precipitating 40 the purified microorganism DNA with an antisolvent. In one embodiment ethanol is used as the antisolvent. This step forms precipitate from the purified solution containing a higher concentration of the microorganism DNA for analysis.

Next, the method 20 continues by dissolving 38 the precipitated microorganism DNA in a buffer solution. In one embodiment, the buffer solution is 50 µl of Tris-EDTA (TE) buffer. The quantity and particular buffer may vary in based on the current conditions. Particularly, other fluid sample types may include additional purification steps as well as other buffers, such as phosphate buffered saline, in order to effectively dissolve the extracted microorganism DNA.

Next, the method 20 amplifies 36 the microorganism DNA from the microorganism cells. This is analogous to step 12 above, but may include additional or different steps as well as appreciated by those of skill in the art.

Next, the method 20 further includes the step of amplification and hybridization of 38 a nucleotide sequence of the extracted microorganism DNA. In another embodiment, this step is conducted through the use of a parallel PCR method. Other PCR methods may also be available for use during this step in the method 20.

Finally, the method further includes the step of amplifying 40 the solution and hybridization to a predetermined second set of genetic markers in order to detect the antibiotic resistance genes of the microorganism represented by the DNA within the solution. In one embodiment, the predetermined second set of genetic markers includes a plurality of antibiotic resistance genes found within sepsis-related microorganisms. In the industrial application of method 20, antibiotic-specific resistant genes most relevant to the hospital setting can be determined by profiling either the Antibiotic Resistant Gene Database with the OpenArray PCR system, or the WaferGen platform (http://www.wafergen.com/alapplications/gene-expression-profiling/) or creating an additional database from obtained results over time. Each sample is tested in technical triplicates. If at least two of the assays are positive, the gene will be determined as present. Resistance gene profiles will be analyzed, interrogating for resistance to certain antibiotics or classes of antibiotics in an effort to identify the drug resistance profile.

In one embodiment, the present disclosure directly addresses the need for fast and accurate diagnosis of offending pathogens in the diagnosis of sepsis. In another embodiment, the present disclosure directly addresses the need for fast and accurate diagnosis of offending pathogens by adapting a POC device to the diagnosis of sepsis. Synergistic implementation of both methods can enable physicians to identify the microorganisms responsible for a patient's septic state in 20 to 30 minutes rather than three days, and reveal an organism's genetic weaknesses in seven hours. This will maximize antibiotic utility, eradicate infection, and help conserve important antibiotics by eliminating the guesswork involved in treating septic patients.

It should be noted that the timeframes mentioned are not meant to be limiting. Although the times of 20 to 30 minutes and 7 hours are used here, the disclosure should not be restricted to any specific time period at this time, but should be viewed as changing the range from several days to a first step in a relatively short waiting time followed by a comprehensive analysis in another longer waiting time, but still relatively shorter than several days. Further, the molecular analyses conducted through these methods tend to be both more accurate and more sensitive than culture-based analysis.

FIG. 3 is a representative table listing the 50 sepsis-related microorganisms that may be identified using method 10. Along with each microorganism is also the associated genetic marker(s) that are used to identify the particular microorganism with the fluid sample. It should be noted that this list is not meant to limiting and can be modified in order to account for additional, relevant microorganisms. As discussed above, FIG. 4 indicates the pathogens as identified with example LAMP primer sequences.

FIG. 5 is a representative output table of the antibiotic resistance analysis conducted through method 20. Along with each identified microorganism are their known antibiotic resistance count, their antibiotic sensitivity count, as well as the analysis and identification of antibiotic gene resistance markers. The identified markers as compared to the prior columns are compared in order to give a percentage of resistance undetected by the identified microorganism.

The order of execution or performance of the operations in the embodiments of the disclosure illustrated and described herein is not essential, unless otherwise specified. That is, the operations described herein may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

Other aspects and features of the present disclosure may be obtained from a study of the drawings, the disclosure, and the appended claims. The methods illustrated within the disclosure may be practiced otherwise than as specifically described within the scope of the appended claims. It should also be noted that the steps and/or functions listed within the appended claims, notwithstanding the order of which steps and/or functions are listed therein, are not limited to any specific order of operation.

Although specific features of various embodiments within the disclosure may be shown in some drawings and not in others, this is for convenience only. In accordance with the principles of the disclosure, any feature of a drawing may be referenced and/or claimed in combination with any feature of any other drawing.

What is claimed is:

1. A method to improve the efficiency of detecting whether sepsis-related microorganisms are present in a fluid sample, the method comprising the steps of:
    collecting the fluid sample from a patient;
    isolating a quantity of microorganism cells from the fluid sample;
    extracting a portion of the microorganism cells from the isolated quantity of the microorganism cells;
    heat lysing the portion of the microorganism cells to extract microorganism DNA therefrom;
    amplifying the microorganism DNA; and
    comparing the amplification of microorganism DNA to a predetermined set of DNA primers to determine whether sepsis-related microorganisms are present within the fluid sample.

2. The method of claim 1, wherein the predetermined set of DNA primers comprises a plurality of genetic markers found within sepsis-related microorganisms.

3. The method of claim 2, wherein the sepsis-related microorganisms are chosen from *Corynebacterium* spp., *Staphylococcus aureus*, Methicillin Resistant *Staphylococcus aureus*, coagulase negative *Staphylococcus epidermidis*, Group A *Streptococcus pyogenes*, Group B *Streptococcus pneumoniae*, *Viridans* group *Streptococcus* spp., *Proteus mirabilis*, *Escherichia coli*, *Klebsiella pneumoniae*, *Enterococcus faecalis*, *Enterococcus faecium*, *Pseudomonas aeruginosa* and *Candida albicans*.

4. The method of claim 1, wherein the step of amplifying the microorganism DNA comprises utilizing a polymerase chain reaction to amplify the microorganism DNA.

5. The method of claim 4, wherein the step of amplifying the microorganism DNA further comprises utilizing an isothermal loop-mediated polymerase chain reaction.

6. The method of claim 5, wherein the isothermal loop-mediated polymerase chain reaction is maintained at a temperature range between 55 to 70 degrees Celsius.

7. The method of claim 4, wherein the step of amplifying the microorganism DNA further comprises amplifying the microorganism DNA to a predetermined concentration within the portion of microorganism cells.

8. The method of claim 7, wherein the predetermined concentration is from 18 cfu/ml to 50 cfu/ml.

9. The method of claim 1, wherein the step of heat lysing the cells is further defined as heat lysing at a temperature of from 60 to 100 degrees Celsius for 1 to 10 minutes.

10. The method of claim 1, wherein the fluid sample is chosen from blood, urine, cerebral spinal fluid, stool, wound, or mucus membrane secretion.

11. The method of claim 1, further comprising the steps of:
    purifying the extracted microorganism DNA;
    precipitating the purified microorganism DNA with an antisolvent; and
    dissolving the precipitated microorganism DNA in a buffer solution; each prior to the step of amplifying the microorganism DNA.

12. A method to improve the efficiency and timing of detecting whether antibiotic-resistant sepsis-related microorganisms are present in a fluid sample, the method comprising the steps of:
    collecting the fluid sample from a patient;
    isolating a quantity of microorganism cells from the fluid sample;
    extracting a portion of the microorganism cells from the isolated quantity of the microorganism cells;
    heat lysing the portion of the microorganism cells to extract microorganism DNA therefrom;
    purifying the microorganism DNA;
    precipitating the purified microorganism DNA with an antisolvent;
    dissolving the precipitated microorganism DNA in a buffer solution;
    amplifying the dissolved microorganism DNA; and
    hybridizing the amplified microorganism DNA to a chip with a predetermined set of genetic markers to determine antibiotic-resistance sepsis-related microorganisms are present within the sample.

13. The method of claim 12, wherein the predetermined set of genetic markers comprises a plurality of antibiotic resistance genes found within sepsis-related microorganisms.

14. The method of claim 1, wherein the step of isolating a quantity of microorganism cells from the fluid sample includes fractioning the fluid sample to isolate the quantity of the microorganism cells from the fluid sample.

* * * * *